US007235699B2

(12) United States Patent
Koch

(10) Patent No.: US 7,235,699 B2
(45) Date of Patent: Jun. 26, 2007

(54) ALKOXY-SUBSTITUTED INDANES AND THE PRODUCTION THEREOF

(75) Inventor: Oskar Koch, Gottingen (DE)

(73) Assignee: Symrise GmbH & Co. KG, Holzminden (DE)

( * ) Notice: Subject to any disclaimer, the term of this patent is extended or adjusted under 35 U.S.C. 154(b) by 151 days.

(21) Appl. No.: 10/506,974

(22) PCT Filed: Feb. 27, 2003

(86) PCT No.: PCT/EP03/01987

§ 371 (c)(1),
(2), (4) Date: Sep. 8, 2004

(87) PCT Pub. No.: WO03/076379

PCT Pub. Date: Sep. 18, 2003

(65) Prior Publication Data

US 2005/0107476 A1    May 19, 2005

(30) Foreign Application Priority Data

Mar. 11, 2002    (DE)    ................................ 102 10 623

(51) Int. Cl.
*C07C 45/33*    (2006.01)
*C07C 41/18*    (2006.01)
(52) U.S. Cl. ...................... 568/320; 568/321; 568/322; 568/327; 568/330; 568/628; 568/632; 568/633
(58) Field of Classification Search ................ 568/320, 568/321, 322, 327, 330, 628, 632, 633
See application file for complete search history.

(56) References Cited

U.S. PATENT DOCUMENTS

| 3,078,319 | A | * | 2/1963 | Wood | ......................... 585/410 |
| 3,681,464 | A | * | 8/1972 | Theimer | ..................... 568/374 |
| 4,277,318 | A | * | 7/1981 | Matlock et al. | ............. 205/447 |
| 4,487,698 | A | * | 12/1984 | Idel et al. | .................... 210/639 |
| 5,426,237 | A | * | 6/1995 | Murahashi et al. | ......... 568/360 |
| 5,965,066 | A | * | 10/1999 | Koch et al. | .................. 252/589 |
| 6,355,842 | B1 | * | 3/2002 | Alsters et al. | .............. 568/312 |
| 2002/0143203 | A1 | | 10/2002 | Koch et al. | |
| 2003/0013603 | A1 | * | 1/2003 | Ishii et al. | .................. 502/167 |

FOREIGN PATENT DOCUMENTS

| EP | 1 000 950 | | 5/2000 |
| JP | 2001-247505 | * | 9/2001 |
| WO | WO 02/38537 | | 5/2002 |

OTHER PUBLICATIONS

Flanagan et al., 1,1,4,6,7-Pentamethylindan, Aug. 1966, J. Org. Chem., vol. 31, No. 8, pp. 2716-2718.*
Pati et al., A stereocontrolled total synthesis of (+−)-norzizanone, Dec. 2000, Tetrahedron Letters, vol. 41, Issue 52, pp. 10353-10356.*
Hirata et al., Screening of an inhibitor of the tetracycline efflux pump in a tetracycline-resistant clinical-isolate of *Staphyloccocus aureus* 743, 1998, vol. 21(7), CAPLUS asbstract.*
Database Crossfire Beilstein 'Online!, Beilstein Institut zur Forderung der Chemischen Wissenschaften, Frankfurt am Main, DE; retreived from XFIRE, Database accession No. 5505898, XP002242444, Zusammenfassung & Bull. Soc. Chim. Belg., Bd. 90, Nr. 8, 1981, pp. 847-848.
Database Crossfire Beilstein 'Online!, Beilstein Institut zur Forderung der Chemischen Wissenschaften, Frankfurt am Main, DE; retreived from XFIRE, Database accession No. 8762625, XP002242445, Zusammenfassung & Bull. Chem. Soc. JP., Bd. 73, Nr. 12, 2000, pp. 2779-2782.
Database Crossfire Beilstein 'Online!, Beilstein Institut zur Forderung der Chemischen Wissenschaften, Frankfurt am Main, DE; retreived from XFIRE, Database accession No. 2209219, XP002242446, Zusammenfassung & J. Amer. Chem. Soc., Bd. 88, 1966, pp. 5809-5816.
Database Crossfire Beilstein 'Online!, Beilstein Institut zur Forderung der Chemischen Wissenschaften, Frankfurt am Main, DE; retreived from XFIRE, Database accession No. 2441487, XP002242447, Zusammenfassung & J. Amer. Chem. Soc., Bd. 102, Nr. 17, 1980, pp. 5618-5626.
Database Crossfire Beilstein 'Online!, Beilstein Institut zur Forderung der Chemischen Wissenschaften, Frankfurt am Main, DE; retreived from XFIRE, Database accession No. 3272305, XP002242457, Zusammenfassung & helv. chim. acta, Bd. 42, 1959, pp. 2111-2117.
Eisenbraun et al.: "Polyalkyl Aromatic Hydrocarbons. II. Cyclialkytation of Benzoid Hydrocarbons with Isoprene", J. Org. Chem., Bd. 33, 1968, pp. 2000-2008, XP002242443.
Database Crossfire Beilstein 'Online!, Beilstein Institut zur Forderung der Chemischen Wissenschaften, Frankfurt am Main, DE; retreived from XFIRE, Database accession No. 2209496, XP002242448, Zusammenfassung & Bull. Soc. Chim. Fr., 1947, pp. 812-815.
Database Crossfire Beilstein 'Online!, Beilstein Institut zur Forderung der Chemischen Wissenschaften, Frankfurt am Main, DE; retreived from XFIRE, Database accession No. 3266549, XP002242451, Zusammenfassung & J. Chem. Soc., 1951, pp. 83-86.
Database Crossfire Beilstein 'Online!, Beilstein Institut zur Forderung der Chemischen Wissenschaften, Frankfurt am Main, DE; retreived from XFIRE, Database accession No. 2372513, XP002242449, Zusammenfassung & TETRAHEDRON, Bd. 30, 1974, pp. 2887-2890.
Database Crossfire Beilstein 'Online!, Beilstein Institut zur Forderung der Chemischen Wissenschaften, Frankfurt am Main, DE; retreived from XFIRE, Database accession No. 2444004, XP002242450, Zusammenfassung & Yakugaku Zasshi, Bd. 76, 1956, pp. 163-166.
Database Crossfire Beilstein 'Online!, Beilstein Institut zur Forderung der Chemischen Wissenschaften, Frankfurt am Main, DE; retreived from XFIRE, Database accession No. 6204342, XP002242452, Zusammenfassung & Z. Naturforsch. B. Anorg. Chem. Org. Chem., Bd. 39, Nr. 12, 1985, pp. 1801-1805.

* cited by examiner

*Primary Examiner*—Rosalynd Keys
(74) *Attorney, Agent, or Firm*—Roylance, Abrams, Berdo & Goodman, L.L.P.

(57)    ABSTRACT

The present invention relates to alkoxy-substituted indanes, their preparation and use and to the preparation and use of the corresponding alkoxy-substituted indanones.

8 Claims, No Drawings

ALKOXY-SUBSTITUTED INDANES AND THE PRODUCTION THEREOF

The present invention relates to alkoxy-substituted indanes, their preparation and use and to the preparation and use of the corresponding alkoxy-substituted indanones.

1-indanones are important intermediates for the preparation of pharmaceutical products (EP-A 421 759 and EP-A 404 536) and of UV-filters (EP-A 823 418, DE-A 10055940.9-44).

The preparation of 1-indanones can be effected by oxidation of correspondingly substituted indanes with oxidising agents such as, for example, oxygen or air in the presence of metal catalysts such as, for example, Co salts (J. prakt. Chem. 334, 373 (1992)).

This oxidation is described, for example, in EP-A 162 465 on the basis of trimethyl- and tetramethyl-indanes with the aid of chromium acetoacetate and cobalt acetoacetate.

Furthermore, such oxidations are also possible with imides such as, for example, N-hydroxy-phthalimide (J. Org. Chem. 60, 3934 (1995)).

The reaction of alkyl-substituted aromatic compounds such as, for example, toluene or xylene (J. Org. Chem. 54, 1418 (1989)) with isoprene are (sic) described in the literature for the preparation of indanes. Phenols or cresols can be reacted analogously, as is described in DE-A 2 603 835, although the yields are low.

Alkoxy-substituted indanes are covered in a broad general formula in EP-A 286 523 and EP-A 807 850, but neither alkoxy-substituted indanes nor the preparation thereof is explicitly described in these publications.

The aim was thus to find a suitable method of preparation for alkoxy-substituted indanes and alkoxy-substituted 1-indanones.

Surprisingly, it has been found that in the reaction with isoprene (2-methyl-1,3-butadiene) alkoxy-substituted aromatic compounds yield considerably better yields than is the case with phenols or cresols.

The present invention relates to alkoxy-substituted indanes of the Formula (II)

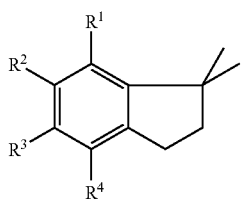

(II)

where
$R^1$, $R^2$, $R^3$ and $R^4$—independently of one another—can be hydrogen, $C_1$-$C_8$-alkyl or $C_1$-$C_8$-alkoxy, with the proviso that at least one of these radicals is $C_1$-$C_8$-alkoxy.

Preferred alkoxy-substituted indanes according to the invention are:

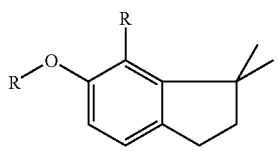

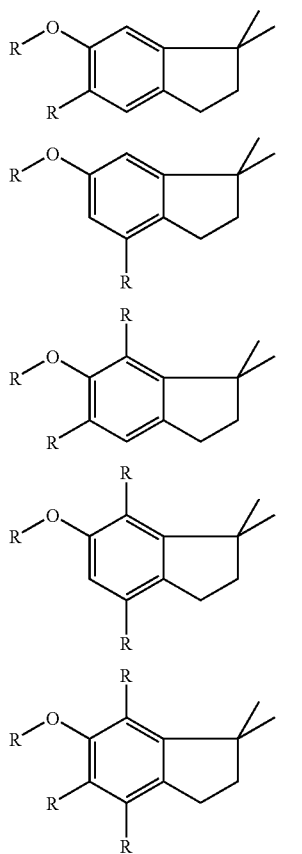

where the substituents R—independently of one another—can denote methyl, ethyl, propyl, i-propyl, n-butyl, i-butyl, tert.-butyl, n-pentyl or i-pentyl.

Particularly preferred compounds are:

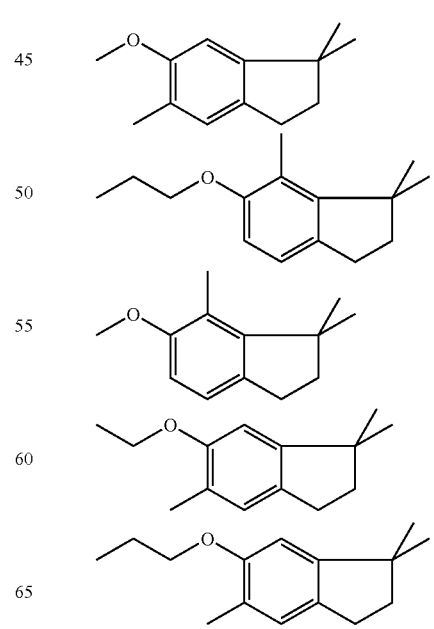

-continued

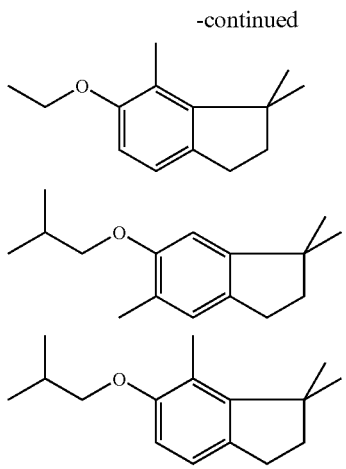

Very particularly preferred compounds are:

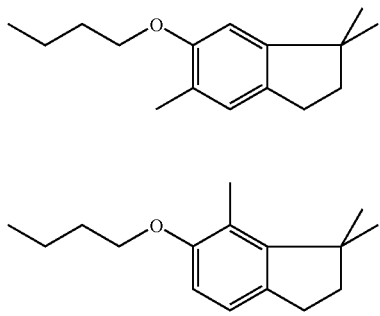

The present invention furthermore relates to the preparation of compounds of the Formula (II) from alkoxy-substituted aromatic compounds of the Formula (I) and isoprene in the presence of an acid catalyst and to the use of the compounds of the Formula (II) for the preparation of the corresponding alkoxy-substituted 1-indanones (III).

The following reaction equation can illustrate the method according to the invention for the preparation of the compounds of the Formula (II):

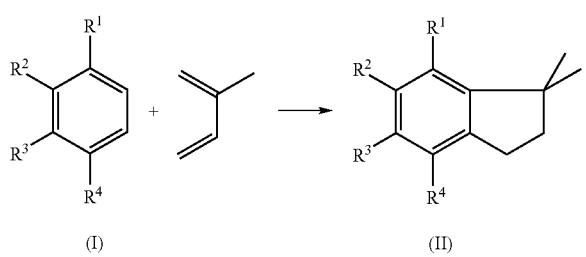

where
$R^1$, $R^2$, $R^3$ and $R^4$—independently of one another—can be hydrogen, $C_1$-$C_8$-alkyl or $C_1$-$C_8$-alkoxy, with the proviso that at least one of these radicals is $C_1$-$C_8$-alkoxy.

Preferred alkoxy-substituted aromatic compounds used according to the invention are:

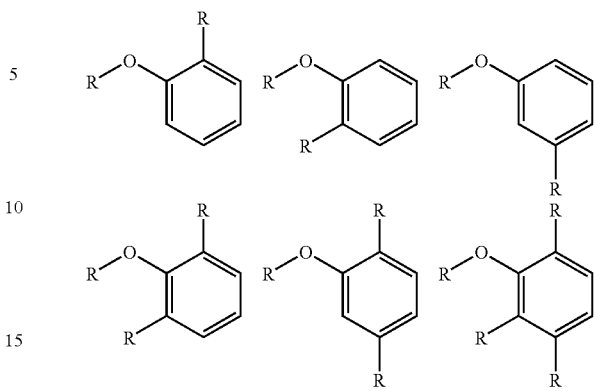

where the substituents R—independently of one another—can denote methyl, ethyl, propyl, i-propyl, n-butyl, i-butyl, tert.-butyl, n-pentyl or i-pentyl.

Particularly preferred alkoxy-substituted aromatic compounds are:

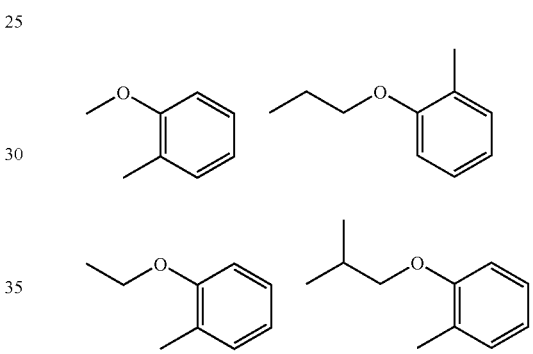

A very particularly preferred compound is:

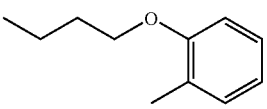

The reaction of the alkoxy-substituted aromatic compounds (I) with isoprene takes place in the presence of acid catalysts. In general, customary Friedel-Crafts catalysts can be used. Acid catalysts that can be used are, for example, inorganic acids, such as phosphoric acid or sulphuric acid, or organic acids such as methanesulphonic acid. Further suitable catalysts are Lewis acids, such as, for example, $AlCl_3$, $ZnCl_2$, $FeCl_3$, $TiCl_4$ and $BF_3$ adducts. The preferred catalyst is sulphuric acid; 70-95% (m/m) sulphuric acid is particularly preferred.

The molar ratio between the alkoxy-substituted aromatic compounds (I) and isoprene is preferably between 7:1 and 1:2, particularly preferentially between 3:1 and 1:1.

The weight-related ratio between the alkoxy-substituted aromatic compounds (I) and sulphuric acid is preferably between 5:1 and 1:1, particularly preferentially between 3:1 and 2:1.

The reaction temperature is advantageously between 0 and 100° C., preferably between 20 and 80° C. and particularly preferentially between 30 and 50° C. The reaction time is advantageously between 10 and 300 min, preferably between 30 and 120 min and particularly preferentially between 40 and 90 min.

The present invention furthermore relates to the preparation of alkoxy-substituted 1-indanones by oxidation of compounds of the Formula (II) and the use of novel alkoxy-substituted 1-indanones for the preparation of pharmaceutical or agrochemical active compounds and for the preparation of UV filters.

The following equation can illustrate the method for the preparation of the alkoxy-substituted 1-indanones of the Formula (III):

where
$R^1$ to $R^4$ have the above mentioned meaning.

In general, this oxidation in the benzyl position can take place in accordance with methods known from the literature.

The oxidation is preferably carried out with oxygen, it also being possible to dilute the oxygen with other gases. Dilution with inert gases is advantageous; oxidation with air is particularly advantageous.

The reaction can be carried out under elevated pressure. Typically, the reaction is carried out under pressures in the range of 1 to 50 bar abs.

This oxidation can be carried out in particular in the presence of compounds of the metals manganese, iron, cobalt, chromium, nickel or copper. Halides, nitrates, sulphates, oxides, acetates or tungstenates of the said metals are preferred. Furthermore, the said metals can be used in the form of complexes with chelate-forming agents such as, for example, acetylacetonates, phthalocyanines, porphyrins, or azaporphyrins. The metal compounds can be used as such or also on supports. Furthermore, the said catalysts can be used on their own or in mixtures.

Preferred metals are nickel, cobalt and copper. Preferred metal compounds are the halides, sulphates, acetates and acetylacetonates. Particularly preferred metal compounds are Co(II) acetate, Co(II) acetylacetonate, Co(III) acetylacetonate, Ni(II) acetate and Ni(II) acetylacetonate.

The amount of metal compound used can be varied within wide ranges and is usually between 0.00001 and 15% (mol/mol), preferably 0.25 to 10% (mol/mol).

This oxidation can also be carried out in the presence of N-hydroxy-imides. Preferred N-hydroxy-imides are N-hydroxy-succinimide, N-hydroxy-maleinimide and N-hydroxy-phthalimide; N-hydroxy-phthalimide is particularly preferred. The amount of N-hydroxy-imides used can be varied within wide ranges and is usually between 0.001 and 15% (mol/mol), preferably 1 to 10% (mol/mol).

It is likewise advantageous to carry out the oxidation in the presence of a compound of the above mentioned metals and a N-hydroxy-imide, preferably a Ni(II), Co(II) or Co(III) compound and N-hydroxy-phthalimide, Co(II) acetate, Co(II) acetyl-acetonate, Co(III) acetylacetonate, Ni(II) acetate and Ni(II) acetylacetonate being preferred.

The reaction temperatures are typically 0 to 200° C., preferably 20 to 120° C., and particularly preferentially 30 to 90° C.

Depending on the consistency of educts or products, an organic diluent can be used. Diluents that can be used are, for example, hydrocarbons, ethers, alcohols, alkyl- or aryl-nitriles as well as organic acids. Lower alcohols, such as, for example, methanol, ethanol or i-propanol, lower organic acids, such as, for example, acetic acid, as well as alkyl- or aryl-nitriles, such as, for example, acetonitrile or benzonitrile, are particularly suitable.

Furthermore, the oxidation can be carried out under the conditions of phase transfer catalysts by adding the above-mentioned metal salts in the form of an aqueous solution to the alkoxy-substituted indanes, which are immiscible with water, with the addition of a phase transfer catalyst. The alkoxy-substituted indanes can be used on their own or in a solvent in this reaction.

Advantageously, the reaction can be carried out, for example, in benzonitrile as organic phase and a solution of Co-(II) chloride, Cu-(II) nitrate and tetrabutylammonium bromide as aqueous phase.

The present invention furthermore relates to novel alkoxy-substituted 1-indanones of the Formula (IV) and to their preparation by the method described above.

(IV)

where
$R^1$, $R^2$ and $R^3$ have the abovementioned meaning.

Preferred alkoxy-substituted 1-indanones are:

The following examples can illustrate the invention:

EXAMPLES

Example 1

3,3,6-trimethyl-5-methoxy-indane and
3,3,4-trimethyl-5-methoxy-indane

-continued

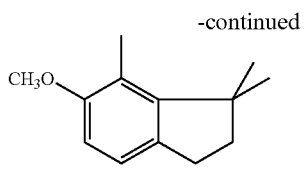

300 g sulphuric acid (85% (m/m)) are initially introduced, with stirring, and a mixture of 732 g o-cresyl methyl ether and 153 g isoprene is added in the course of 50 min. During this addition, the temperature is kept to a maximum of 30° C. by cooling. The reaction mixture is stirred for a further 20 min at this temperature, 400 g water is added, the phases are separated and washed with sodium bicarbonate until neutral. After distilling off the excess o-cresyl methyl ether, 300 g of the mixture of isomers (ratio 3:1) is obtained, which corresponds to a yield of 70% of theory.

The two isomers are separated by distillation in a 1 m packed column and can be used individually for the oxidation.

Example 2

3,3,6-trimethyl-5-butoxy-indane and 3,3,4-trimethyl-5-butoxy-indane

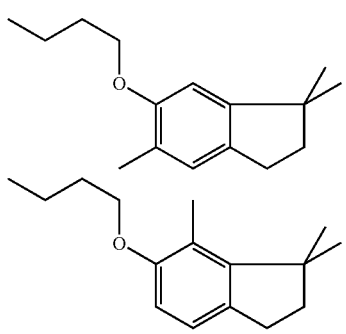

The reaction is carried out analogously to Example 1, o-cresyl butyl ether being employed. The yield is 70% of theory.

Preparation of 2-methyl-butoxy-benzene (o-cresyl Butyl Ether)

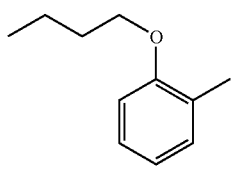

540 g (5.0 mol) o-cresol, 500 g n-butanol and 560 g (5.0 mol) 50% (m/m) potassium hydroxide solution are initially introduced and heated under reflux, the water being removed azeotropically. 463 g (5.0 mol) n-butyl chloride are then metered in under reflux in the course of 2 h, further water being cycled out. After metering, the reaction mixture is stirred for a further 2 h, cooled to 80° C., hydrolysed with 800 g water and adjusted to pH 4 with 50% (m/m) sulphuric acid. The phases are separated at 70° C. After distillation, 794 g product with a purity of 94% is obtained.

Yield: 90% of theory.

Example 3

3,3,6-trimethyl-5-butoxy-indan-1-one

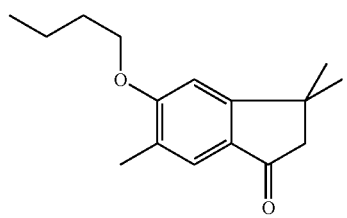

100 g 3,3,6-trimethyl-5-butoxy-indane are dissolved in 400 g acetic acid and 1 g Co-II acetate is added. The reaction mixture is heated to 40° C., with stirring, and oxygen is passed through this solution for 10 hours. After cooling to room temperature, 500 g water and 500 g methyl tert.-butyl ether are added. After phase separation, the organic phase is rinsed with a further 200 g water and distilled in a 30 cm packed column. 80 g 3,3,6-trimethyl-5-butoxy-indan-1-one is obtained, which corresponds to a yield of 75% of theory. The compound can be recrystallised from heptane and a white solid is obtained, melting point: 59° C.

Example 4

3,3,4-trimethyl-5-butoxy-indan-1-one

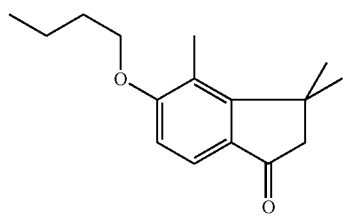

The reaction is carried out analogously to Example 3, 3,3,4-trimethyl-5-butoxy-indane being employed. The yield is 70% of theory.

The invention claimed is:

1. A method for the preparation of compounds having the formula

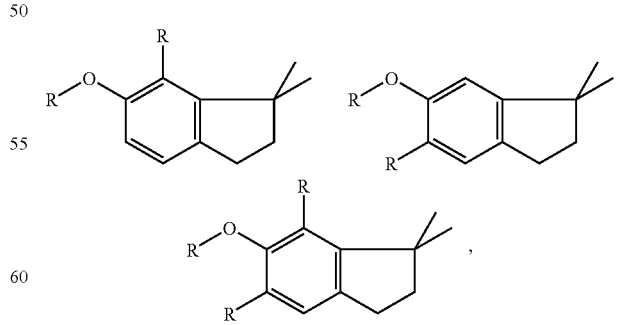

said method comprising reacting an alkoxy substituted aromatic compound with isoprene in the presence of an acid catalyst, wherein said alkoxyl substituted aromatic compound has the formula:

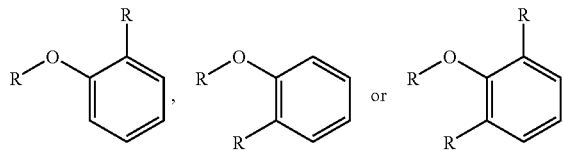

wherein R is independently selected from the group consisting of methyl, ethyl, propyl, i-propyl, n-butyl, i-butyl, tert-butyl, n-pentyl and i-pentyl.

2. A method for the preparation of compounds of the formulas

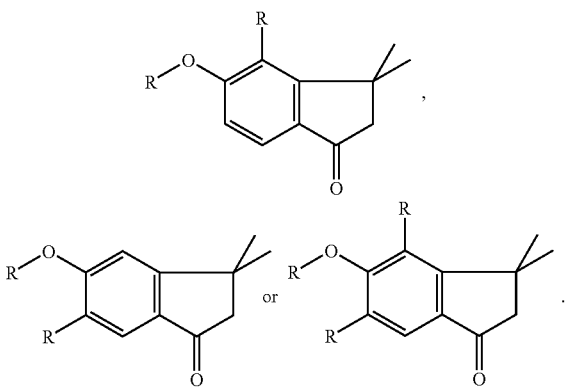

wherein R is independently selected from the group consisting of methyl, ethyl, propyl, i-propyl, n-butyl, i-butyl, tert-butyl, n-pentyl and i-pentyl, said method comprising the step of oxidizing a compound of formulas

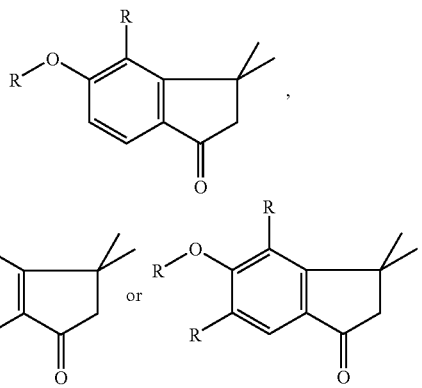

3. The method according to claim 2, wherein the oxidation is carried out using oxygen as an oxidizing agent.

4. The method according to claim 3, wherein the oxidation is carried out in the presence of a metal compound, where the metal is selected from the group consisting of manganese, iron, cobalt, chromium, nickel and copper.

5. The method according to claim 3, wherein the oxidation is carried out in the presence of an N-hydroxy-imide.

6. The method according to claim 3, wherein the oxidation is carried out with the aid of phase transfer catalysis.

7. The method according to claim 4, wherein the oxidation is carried out in the presence of an N-hydroxy-imide.

8. The method according to claim 2, wherein the oxidation is carried out with the aid of phase transfer catalysis.

* * * * *